United States Patent [19]

Yoshida

[11] Patent Number: 5,526,813
[45] Date of Patent: Jun. 18, 1996

[54] METHOD AND APPARATUS FOR HEART BEAT SYNCHRONOUS NUCLEAR MAGNETIC RESONANCE IMAGING

[75] Inventor: Tomoyuki Yoshida, Ootawara, Japan

[73] Assignee: Kabushiki Kaisha Toshiba, Kanagawa-ken, Japan

[21] Appl. No.: 231,585

[22] Filed: Apr. 20, 1994

Related U.S. Application Data

[63] Continuation of Ser. No. 978,038, Nov. 18, 1992, abandoned, which is a continuation of Ser. No. 649,892, Feb. 4, 1991, abandoned.

[30] Foreign Application Priority Data

Feb. 5, 1990 [JP] Japan ............................ 2-25464

[51] Int. Cl.$^6$ ........................................ A61B 5/055
[52] U.S. Cl. ..................... 128/653.2; 128/708; 128/901
[58] Field of Search .................. 128/653.2, 653.5, 128/653.3, 696, 708, 901

[56] References Cited

U.S. PATENT DOCUMENTS

| | | | |
|---|---|---|---|
| 4,602,641 | 7/1986 | Feinberg | 128/653 AF |
| 4,796,635 | 1/1989 | Dumoulin | 128/653 AF |
| 4,958,637 | 9/1990 | Aritomi | 128/653 A |
| 4,961,426 | 10/1990 | Spraggins et al. | 128/653 A |
| 5,038,785 | 8/1991 | Blakeley et al. | 128/653 A |

*Primary Examiner*—Ruth S. Smith
*Attorney, Agent, or Firm*—Ronald L. Yin; Limbach & Limbach

[57] ABSTRACT

A method and an apparatus for heart beat synchronous nuclear magnetic resonance imaging capable of improving the quality of the nuclear magnetic resonance images synchronous with the heart beat by reducing erroneous generation of synchronization signals due to noises in the electro-cardiographic waves. In the apparatus, noises are removed from the electro-cardiographic waves obtained from the patient; synchronization signals are generated in correspondence to the noise removed electro-cardiographic waves; and nuclear magnetic resonance images are taken by collecting nuclear magnetic resonance signals from the patient at collection timings determined in correspondence to the synchronization signals, and by reconstructing the nuclear magnetic resonance images by using the collected nuclear magnetic resonance signals.

10 Claims, 6 Drawing Sheets

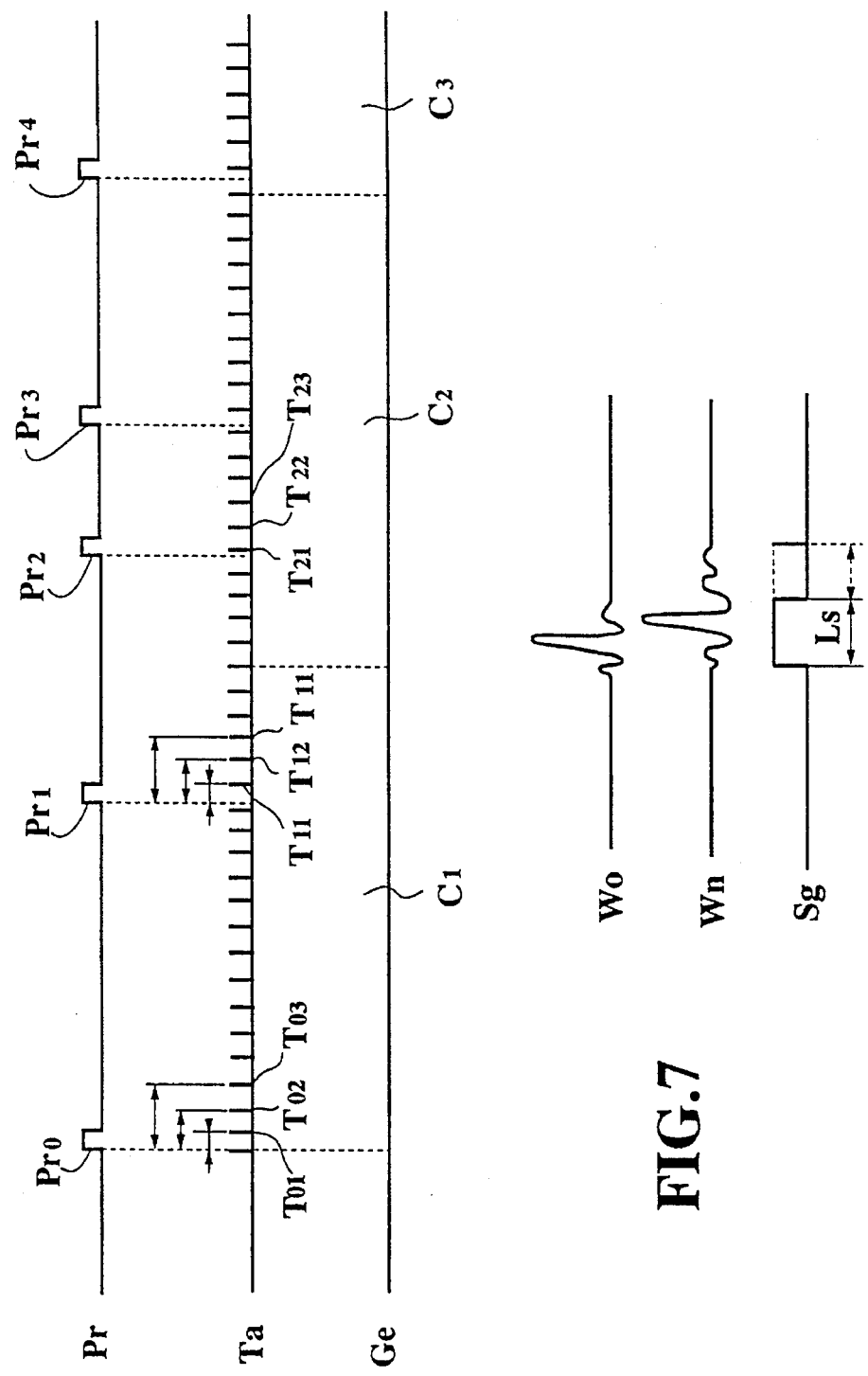

METHOD AND APPARATUS FOR HEART BEAT SYNCHRONOUS NUCLEAR MAGNETIC RESONANCE IMAGING

This is a continuation of application Ser. No. 07/978,038 filed on Nov. 18, 1992, now abandoned which is a continuation of 07/649,892 filed on Feb. 4, 1991, now abandoned.

BACKGROUND OF THE INVENTION

1. Field of the Invention

The present invention relates to a method and an apparatus for nuclear magnetic resonance imaging for taking nuclear magnetic resonance images which are synchronous to the heart beat of a patient.

2. Description of the Background Art

In a conventional nuclear magnetic resonance imaging apparatus, the nuclear magnetic resonance images synchronous to the heart beat of a patient have been obtained by taking the electro-cardiogram of the patient, and generating synchronization signals such as QRS pulses Pr which are synchronized with the rise of the R wave, such that the nuclear magnetic resonance imaging is carried out by using the generated synchronization signals.

For example, in a case of taking the nuclear magnetic resonance images of the heart of the patient, the RF pulses are applied onto the patient in synchronization with the generated QRS pulses Pr, such that the nuclear magnetic resonance signals at different time sequence phases are collected with the QRS pulses Pr as the reference. Then, the nuclear magnetic resonance signals corresponding to each time sequence phase are selected from the collected nuclear magnetic resonance signals, such that the nuclear magnetic resonance image at each time sequence phase can be reconstructed and displayed.

However, as shown in FIG. 1, when the RF pulses are applied, the RF noises Wn are introduced into the electro-cardiographic wave Wh. As a result, not only the QRS pulses Pr are generated in response to the genuine electro-cardiographic wave Wh, but also the additional pulses Pr' are generated in response to these RF noises Wn. Moreover, this generation of the additional pulses Pr' occurs within the scanning interval Ts during which the nuclear magnetic resonance signals are collected, so that the synchronization of the nuclear magnetic resonance signals with the heart beat is disturbed and the quality of the reconstructed nuclear magnetic resonance images are deteriorated.

SUMMARY OF THE INVENTION

It is therefore an object of the present invention to provide a method and an apparatus for heart beat synchronous nuclear magnetic resonance imaging capable of improving the quality of the nuclear magnetic resonance images synchronous with the heart beat by reducing erroneous generation of synchronization signals due to noises in the electro-cardiographic waves.

According to one aspect of the present invention there is provided a nuclear magnetic resonance imaging apparatus, comprising: electro-cardiogram means for obtaining electro-cardiographic waves from a patient; noise removal means for removing externally introduced noises from the electro-cardiographic waves in order to obtain noise removed electro-cardiographic waves; synchronization means for generating synchronization signals in correspondence to the noise removed electro-cardiographic waves; and imaging means for taking nuclear magnetic resonance images by collecting nuclear magnetic resonance signals from the patient at collection timings determined in correspondence to the synchronization signals, and by reconstructing the nuclear magnetic resonance images by using the collected nuclear magnetic resonance signals.

According to another aspect of the present invention there is provided a method of nuclear magnetic resonance imaging, comprising the steps of: obtaining electro-cardiographic waves from a patient; removing externally introduced noises from the electro-cardiographic waves in order to obtain noise removed electro-cardiographic waves; generating synchronization signals in correspondence to the noise removed electro-cardiographic waves; and taking nuclear magnetic resonance images by collecting nuclear magnetic resonance signals from the patient at collection timings determined in correspondence to the synchronization signals, and by reconstructing the nuclear magnetic resonance images by using the collected nuclear magnetic resonance signals.

Other features and advantages of the present invention will become apparent from the following description taken in conjunction with the accompanying drawings.

BRIEF DESCRIPTION OF THE DRAWINGS

FIG. 6 is a timing chart for signals in the apparatus of FIG. 2, for explaining a generation of a discrimination information used in the apparatus of FIG. 2.

FIG. 7 is a timing chart of one possible state of signals in the apparatus of FIG. 2, for explaining one modification of the apparatus of FIG. 2.

DETAILED DESCRIPTION OF THE PREFERRED EMBODIMENTS

Figure 1:
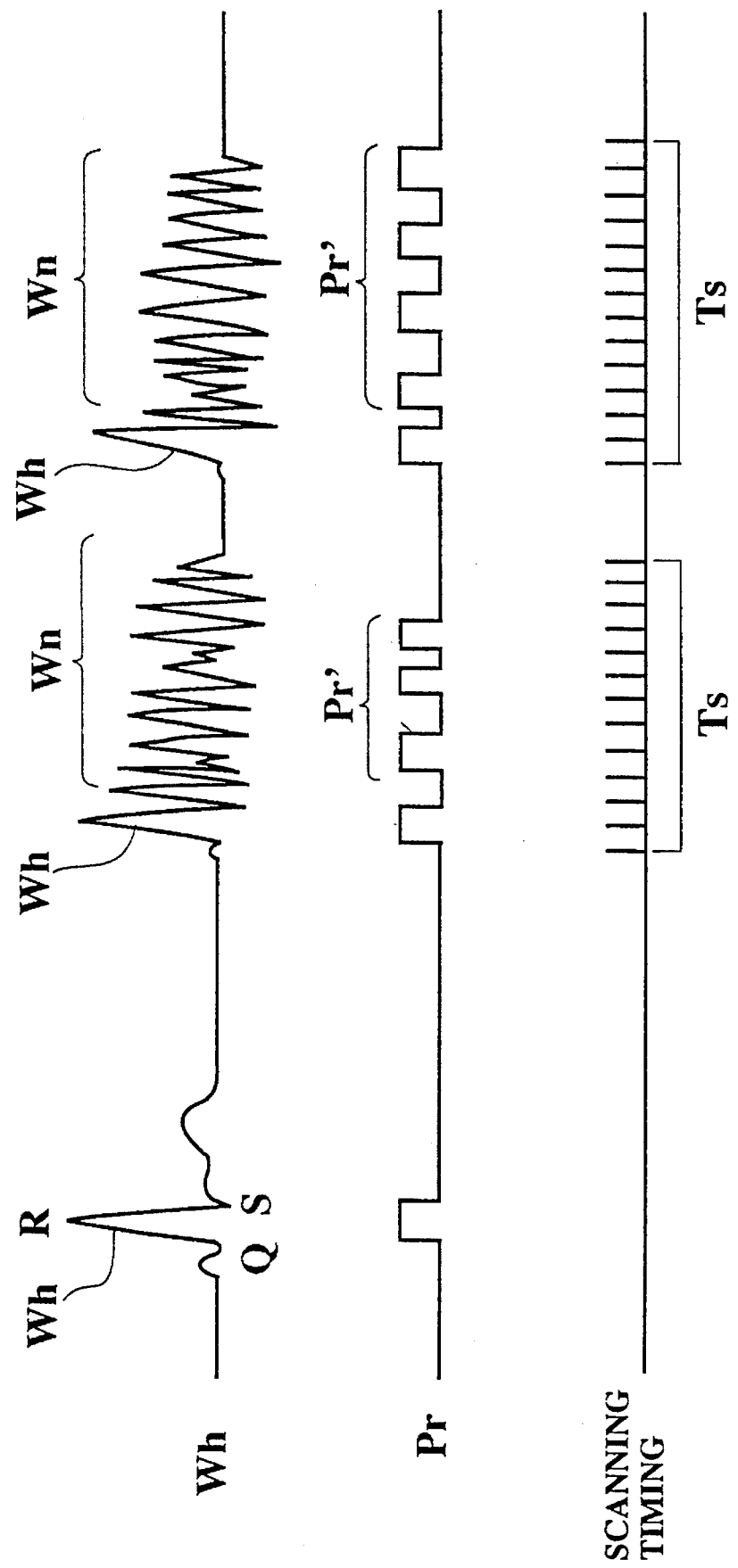
FIG. 1 is a graph of an electro-cardiographic wave, QRS pulses, and scanning timing in a conventional heart beat synchronous nuclear magnetic resonance imaging.
Figure 2:
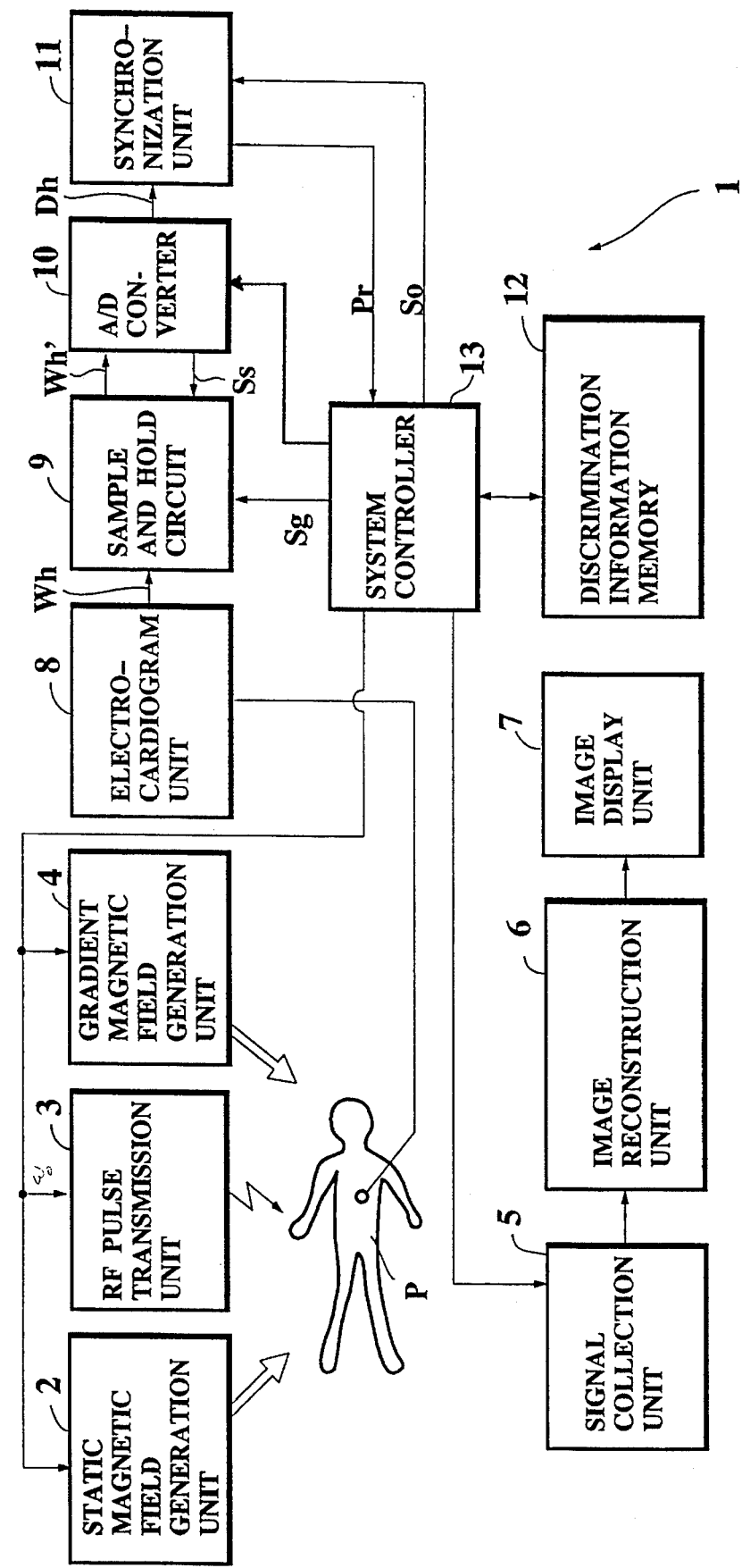
FIG. 2 is a block diagram of one embodiment of a heart beat synchronous nuclear magnetic resonance imaging apparatus according to the present invention.

Referring now to FIG. 2, one embodiment of a heart beat synchronous nuclear magnetic resonance imaging apparatus according to the present invention will be described.

In this embodiment, the apparatus 1 comprises: a static magnetic field generation unit 2 for generating a static magnetic field in a region surrounding a patient P; an RF pulse transmission unit 8 including an RF amplifier (not shown) for applying RF pulses of 3 to 10 ms period onto the patient P; a gradient magnetic field generation unit 4 for generating a slicing gradient magnetic field Gs, an encoding gradient magnetic field Ge, and a reading gradient magnetic field Gr which are orthogonal each other and are superposed onto the static magnetic field; a signal collection unit 5 for collecting nuclear magnetic resonance signals from the patient P; an image reconstruction unit 6 for reconstructing nuclear magnetic resonance images from the collected nuclear magnetic resonance signals by using two-dimensional Fourier transform; an image display unit 7 for displaying the reconstructed nuclear magnetic resonance images; an electro-cardiogram unit 8 for taking the electro-cardiographic waves Wh from the patient P; an sample and hold circuit 9 for removing noises Wn such as RF noises from the electro-cardiographic waves Wh by performing the sampling and holding operation in order to obtain noise removed electro-cardiographic waves Wh'; an A/D converter 10 for converting the noise removed electro-cardiographic waves Wh' into digital signals Dh; a synchronization unit 11 for producing QRS pulses Pr as the synchronization signals according to the digital signals Dh; discrimination information memory 12 for recording discrimination information for the nuclear magnetic resonance imaging signals collected by the signal collection unit 5; and a system controller 13 for controlling operations of the aforementioned elements of the apparatus 1. The A/D converter 10 also supplies status signals Ss to be utilized by the sample and hold circuit 9, while the system controller 13 also supplies gate signals Sg to be utilized by the sample and hold circuit 9 and synchronization request signals So for activating the production of the QRS pulses Pr from the synchronization unit 11.

Figure 3:
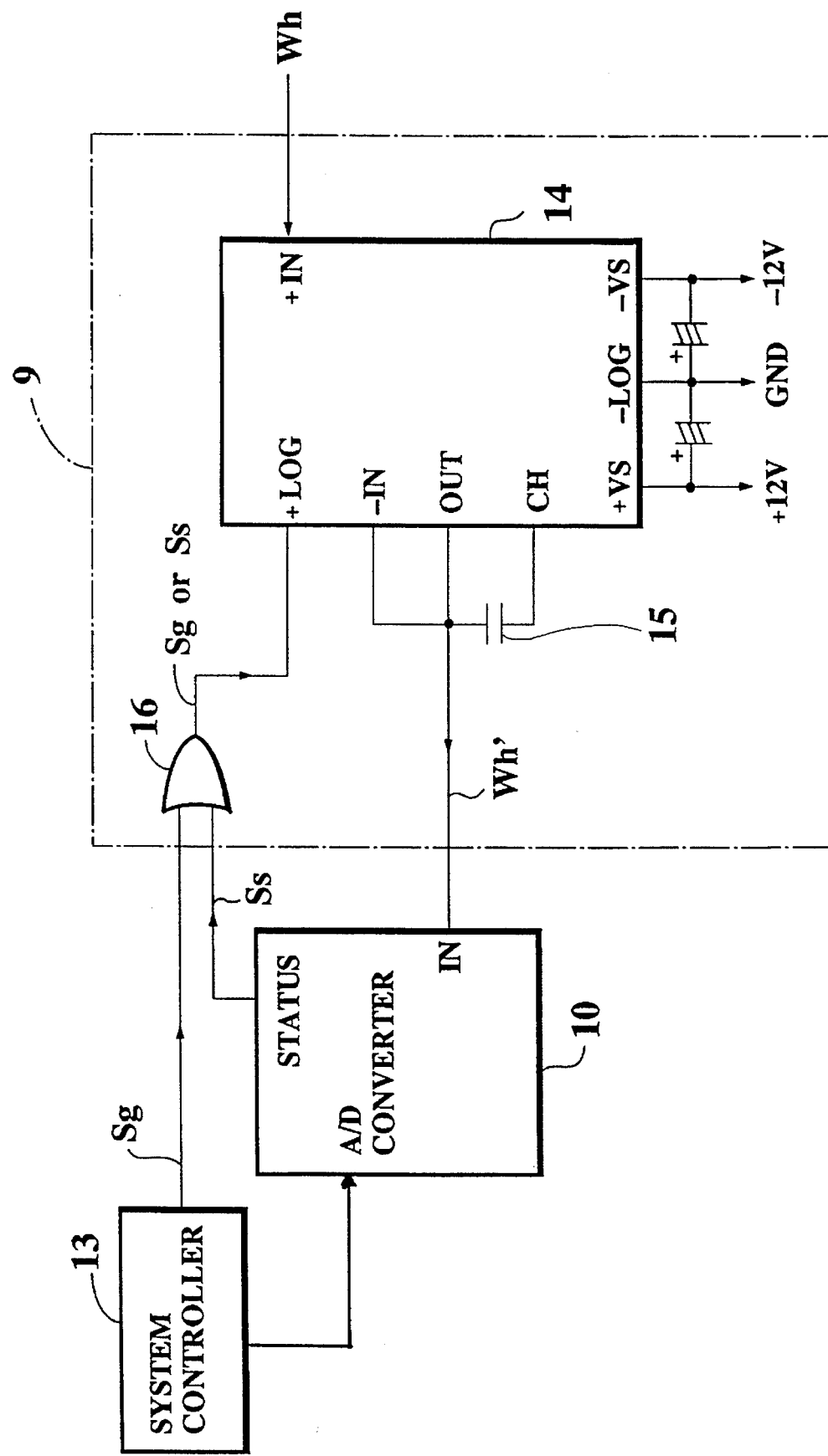
FIG. 3 is a block diagram of a sample and hold circuit used in the apparatus of FIG. 2.

The sample and hold circuit 9 has a configuration shown in FIG. 3. Namely, this sample and hold circuit 9 comprises a sample and hold element 14, a capacitor 15 to be utilized in hold operations, and an OR element 16 to which the status signals Ss from the A/D converter 10 and the gate signals Sg from the system controller 13 are entered. The sample and hold element 14 receives the electro-cardiographic waves Wh from the electro-cardiogram unit 8 and one of the status signals Ss and the gate signals Sg from the OR element 16, and outputs the noise removed electro-cardiographic waves Wh' as follows.

First, the system controller 13 transmits source Rf pulses $W_0$ to the RF pulse transmission unit 3, such that the RF pulse transmission unit 3 can transmit the RF pulses obtained by amplifying the source RF pulses at the RF amplifier. At the same time, the system controller 13 also controls the A/D converter 10 to transmit the status signals Ss to the OR element 16 during the period of scanning in which the nuclear magnetic resonance signals are collected by the signal collection unit 5, while the system controller 13 itself is transmitting the gate signals Sg to the OR element 16 in correspondence to the transmission of the source RF pulses $W_0$ to the RF pulse transmission unit 3. The OR element 16 outputs the gate signals Sg to the +LOG terminal of the sample and hold element 14 while both of the gate signals Sg and the status signals Ss are inputted. Otherwise, the OR element 16 outputs the status signals Ss to the +LOG terminal of the sample and hold element 14. The sample and hold element 14 holds the electro-cardiographic waves Wh while the gate signals Sg are entered to the +LOG terminal, and samples the electro-cardiographic waves Wh otherwise, such that the noises can be removed from the electro-cardiographic waves Wh by holding during the noises.

Figure 4:
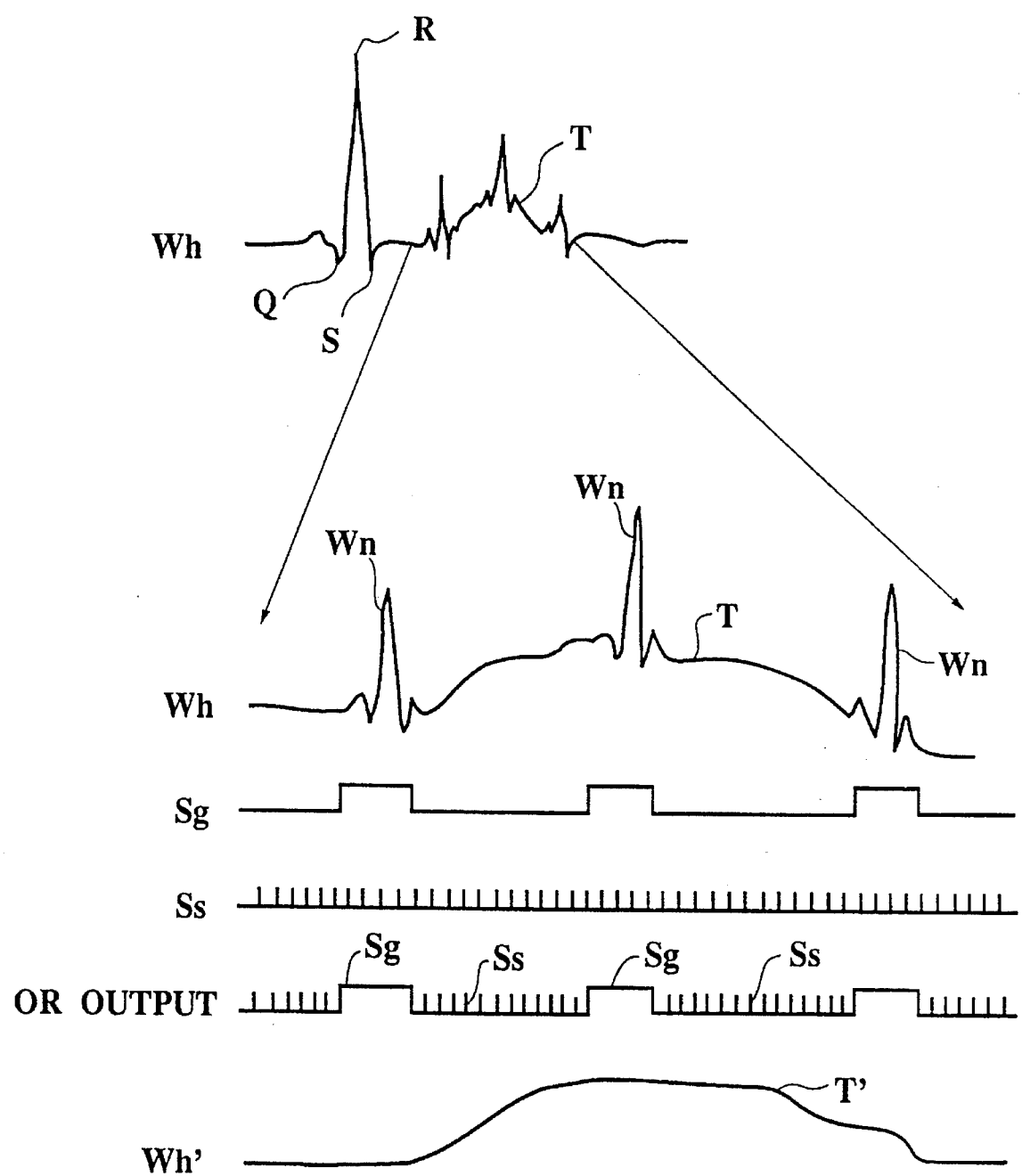
FIG. 4 is a timing chart for various signals in the sample and hold circuit of FIG. 3.

For example, as shown in FIG. 4, when the electro-cardiographic waves Wh obtained by the electro-cardiogram unit 8 has Q wave, R wave, S wave, and T wave, and the RF noises Wn are mixed with the T wave, a period of time for holding the electro-cardiographic waves Wh is set to be 3 to 10 ms which is in correspondence to a period of generation of the RF noises Wn and which is sufficiently shorter than a time interval of 80 to 100 ms between the Q and S waves. In this manner, the sample and hold circuit 9 can output the noise removed electro-cardiographic waves Wh' in which the QRS pulses Pr can be reproduced in sufficient accuracy while obtaining the noise removed T wave T' in which the RF noises Wn are absent.

Figure 5:
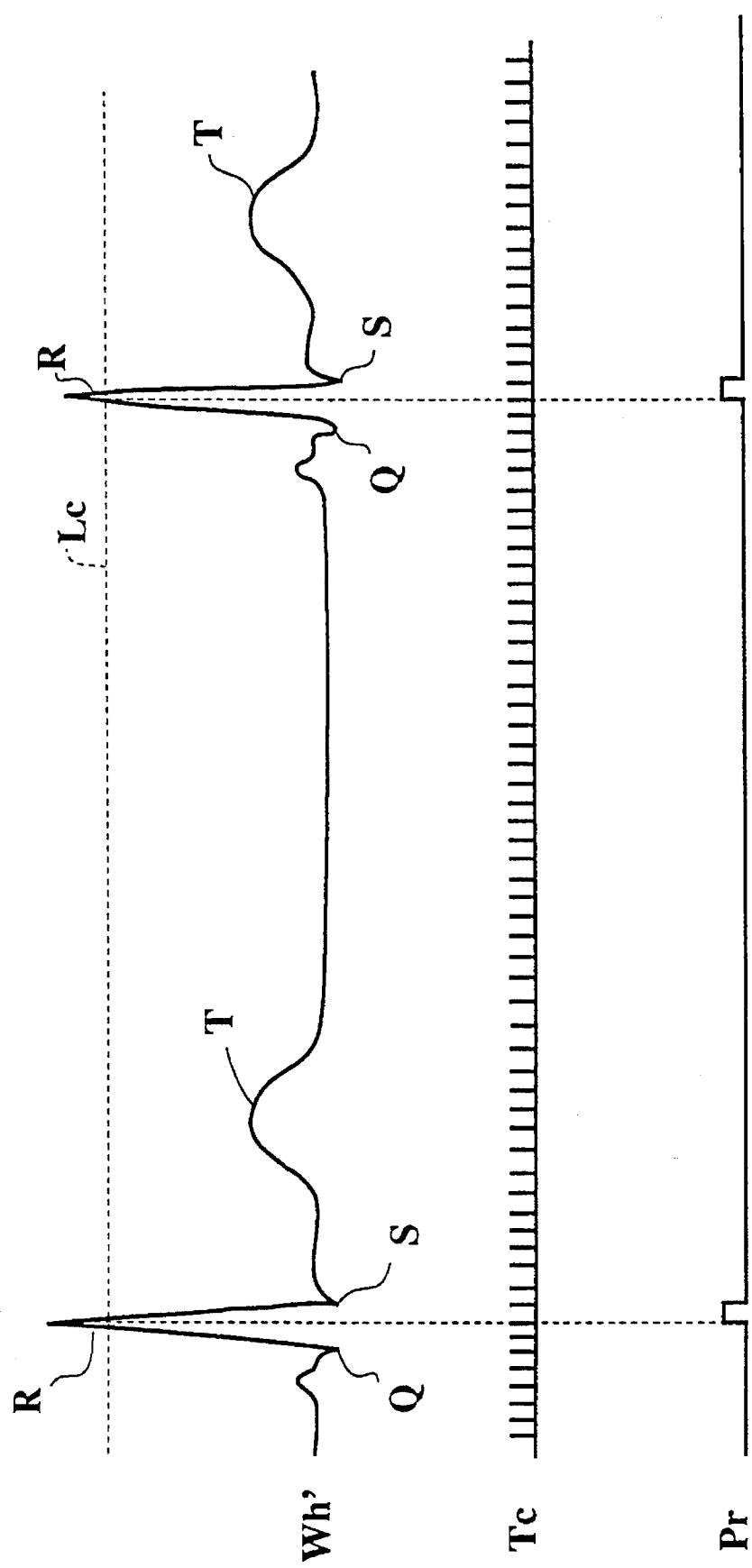
FIG. 5 is a timing chart for signals in a synchronization unit used in the apparatus of FIG. 2, for explaining a generation of synchronization signals.

The synchronization unit 11 compares output levels of the digital signals Dh obtained from the noise removed electro-cardiographic waves Wh' at the A/D converter 10 with a prescribed comparator level Lc. Then, when the synchronization request signals $S_0$ are transmitted from the system controller 13, the synchronization unit 11 picks out the timings at which the output levels of the digital signals Dh exceeds the comparator level Lc as the timings of the R waves, and outputs the QRS pulses Pr when the timings of the R waves coincide with the A/D conversion timings Tc as shown in FIG. 5. In FIG. 5, the analog form of the noise removed electro-cardiographic waves Wh' is depicted along with the comparator level Lc for the sake of easy visual comprehension, although this comparison is actually carried out in terms of the digital signals Dh and the comparator level Lc digitally.

In this embodiment, the system controller 13 operates in a so called non-gate mode in which the system controller 13 provides the pulse sequence of constant intervals which is synchronized with the first one of the QRS pulses Pr from the synchronization unit 11 but not synchronized with any subsequent QRS pulses Pr, such that the nuclear magnetic resonance signals can be collected consecutively at constant intervals of 30 ms for example.

The discrimination information memory 12 memorizes the discrimination information for the nuclear magnetic resonance signals which are collected by the signal collection unit 5 under different conditions.

Namely, as shown in FIG. 6, when the QRS pulses Pr are transmitted to the system controller 13 in correspondence to the R waves of the electro-cardiographic waves Wh, a counter in the system controller 13 measures a time for each signal collection timing with respect to each QRS pulse Pr, and the system controller 13 controls the discrimination information memory 12 to memorize the measured time for each timing, an order of this timing among the collection timings, and the encode condition in this timing.

For example, when the first timing $T_{01}$ with respect to the 0-th QRS pulse $Pr_0$ is measured to be 30 ms which is equal to the collection timing interval Ta, the time for the second timing $T_{02}$ is measured as 60 ms and so on, and the measured time and the order of the timing are memorized in the discrimination information memory 12 along with the relevant encode condition $C_1$ such as the encoding gradient magnetic field strength Ge, while the nuclear magnetic resonance signals are collected at the timings $T_{01}$, $T_{02}$, etc., and recorded by the signal collection unit 5.

Then, when the first QRS pulse $Pr_1$ is transmitted to the system controller 13, the counter in the system controller 13 is reset, and a time for each signal collection timing with respect to this QRS pulse $Pr_1$ is measured by this counter. Here, for example, if the first timing $T_{11}$ with respect to the first QRS pulse $Pr_1$ is measured to be 20 ms which is not equal to the collection timing interval Ta, the time for the second timing $T_{12}$ is measured as 50 ms and so on, and the measured time and the order of the timing are memorized in the discrimination information memory 12 along with the relevant encode condition $C_1$ such as the encoding gradient magnetic field strength Ge which remains the same in this case, while the nuclear magnetic resonance signals are collected at the timings $T_{11}$, $T_{12}$, etc., and recorded by the signal collection unit 5. Similarly if the first timing $T_{21}$ with respect to the second QRS pulse $Pr_2$ is measured to be 10 ms which is not equal to the collection timing interval Ta, the time for the second timing $T_{22}$ is measured as 40 ms and so on, and and the measured time and the order of the timing are memorized in the discrimination information memory 12 along with the relevant encode condition $C_2$ such as the encoding gradient magnetic field strength Ge which is changed in this case, while the nuclear magnetic resonance signals are collected at the timings $T_{01}$, $T_{02}$, etc., and recorded by the signal collection unit 5.

In this manner, the time for the collection timings $T_{01}$, $T_{02}$, —, $T_{11}$, $T_{12}$, —, $T_{21}$, $T_{22}$, —with respect to the QRS pulses $Pr_0$, $Pr_1$, $Pr_2$, —are measured and are memorized along with the relevant encode conditions $C_1$, $C_2$, $C_3$, —.

As a result, those nuclear magnetic resonance signals which are collected at the collection timings of the same order with respect to the QRS pulses $Pr_0$, $Pr_1$, $Pr_2$, —, or those nuclear magnetic resonance signals which are collected at the timings for which the measured times are sufficiently close to each other, can be considered as those belonging to the same heart beat phase. Namely, those nuclear magnetic resonance imaging signals which are collected at the collection timings $T_{01}$, $T_{11}$, $T_{21}$, —, belong to the same heart beat phase, and those nuclear magnetic resonance imaging signals which are collected at the collection timings $T_{02}$, $T_{12}$, $T_{22}$, —, belong to the same heart beat phase.

Thus, in obtaining the nuclear magnetic resonance image of a particular heart beat phase, the system controller 13 searches out the discrimination information corresponding to the nuclear magnetic resonance signals belonging to that particular heart beat phase in the discrimination information memory 12 and transmits the searched out discrimination information to the signal collection unit 5. In response, the signal collection unit 5 selects out the nuclear magnetic resonance signals for that particular heart beat phase from all the collected nuclear magnetic resonance signals, and transmits the selected out nuclear magnetic resonance signals to the image reconstruction unit 6, such that the image reconstruction unit 6 can reconstruct the nuclear magnetic resonance image for that particular heart beat phase.

Next, the overall operation of the heart beat synchronous nuclear magnetic resonance imaging apparatus 1 of FIG. 2 will be described for an exemplary case of imaging a heart of the patient P.

First, the patient P is placed inside the static magnetic field generated under the control of the system controller 13 by the static magnetic field generation unit 2, and a detection electrode of the electro-cardiogram unit 8 is attached to the patient P.

Then, the system controller 13 controls the apparatus 1 to execute the prescribed pulse sequence. Namely, the system controller 13 controls the gradient magnetic field generation unit 4 first in order to superpose the slicing gradient magnetic field Gs to the static magnetic field, and then the RF pulse transmission unit 3 in order to apply the RF pulses which selectively excite the nuclei in the heart of the patient P. Then, under the control of the system controller 13, the gradient magnetic field generation unit 4 superposes the reading gradient magnetic field Gr and the encoding gradient magnetic field Ge of the first encode condition $C_1$ to the static magnetic field, while the RF pulse transmission unit 3 repeats the application of the RF pulses at prescribed constant interval.

Next, the signal collection unit 5 collects the nuclear magnetic resonance signals from the heart of the patient P at the constant collection timings Ta. On the other hand, the electro-cardiogram unit 8 detects the electro-cardiographic waves Wh from the heart of the patient P through the detection electrode and transmits the detected electro-cardiographic waves Wh to the sample and hold circuit 9.

The sample and hold circuit 9 holds the electro-cardiographic waves Wh while the gate signals Sg are transmitted from the system controller 13, and samples the electro-cardiographic waves Wh otherwise, so as to output the noise removed electro-cardiographic waves Wh' to the A/D converter 10, as described above. The noise removed electro-cardiographic waves Wh' are then converted into the digital signals Dh at the A/D converter 10, and the synchronization unit 11 transmits the QRS pulses Pr to the system controller 13 on a basis of the detection of the R waves in the digital signals Dh as described above.

The system controller 13 then controls the discrimination information memory 12 to memorize the discrimination information for the nuclear magnetic resonance signals collected by the signal collection unit 5 in the manner described above. The encode condition is changed among various conditions $C_1$, $C_2$, etc. for a prescribed number of times such as 128 times during the collection of the nuclear magnetic resonance signals by the signal collection unit 5.

After the collection of the nuclear magnetic resonance signals is completed, the system controller 13 searches out the discrimination information corresponding to the nuclear magnetic resonance signals belonging to a particular heart beat phase in the discrimination information memory 12 and transmits the searched out discrimination information to the signal collection unit 5. In response, the signal collection unit 5 selects out the nuclear magnetic resonance signals for that particular heart beat phase from all the collected nuclear magnetic resonance signals, and transmits the selected out nuclear magnetic resonance signals to the image reconstruction unit 6. The image reconstruction unit 6 then reconstructs the nuclear magnetic resonance image for that particular heart beat phase, and the image display unit 7 displays the reconstructed nuclear magnetic resonance image for that particular heart beat phase.

Thus, according to this embodiment, even when the noises such as the RF noises are introduced into the electro-cardiographic waves, the noises can be removed by the proper operation of the sample and hold circuit 9, so that very accurate generation of the QRS pulses becomes possible. In addition, the nuclear magnetic resonance signals of different heart beat phases are discriminated by using the QRS pulses as references, so that accurately synchronized nuclear magnetic resonance image can be obtained for each heart beat phase, even when the patient P is irregularly pulsating.

It is to be noted that, by the application of the present invention, the noises other than the RF noises such as those due to the gradient magnetic field amplifiers can also be dealt with in the manner similar to that described for the above embodiment.

It is also to be noted that although the system controller 13 in the above embodiment has been described as operating in the non-gate mode, the pulse sequence which is completely synchronized with the QRS pulses may be employed instead.

It is further to be noted that the sample and hold circuit in the above embodiment may be replaced by a microcomputer programmed to simulate the operation of the sample and hold circuit.

Furthermore, although the gate signals Sg are transmitted in correspondence to the generation of the source RF pulses $W_0$ in the above embodiment, in a case shown in FIG. 7 in which the tall of the RF noises Wn is extending beyond the signal width Ls of the gate signals Sg, the signal width Ls of the gate signals Sg may be extended in correspondence to the extending tall of the RF noises Wn as indicated by dashed line in FIG. 7.

Besides these, many modifications and variations of the above embodiments may be made without departing from the novel and advantageous features of the present invention. Accordingly, all such modifications and variations are intended to be included within the scope of the appended claims.

What is claimed is:

1. A nuclear magnetic resonance imaging apparatus, comprising:

electro-cardiogram means for obtaining electro-cardiographic waves from a patient;

noise removal means for removing external noises from the electro-cardiographic waves by operating on the electro-cardiographic waves to obtain noise removed electro-cardiographic waves;

synchronization means for generating synchronization signals in correspondence to the noise removed electro-cardiographic waves;

imaging means for taking nuclear magnetic resonance images by collecting nuclear magnetic resonance signals from the patient at collection timings determined in correspondence to the synchronization signals, and by reconstructing the nuclear magnetic resonance images by using the collected nuclear magnetic resonance signals; and sequence controller means for controlling the imaging means for taking the nuclear magnetic resonance images in a prescribed sequence in which the external noises are generated at known timings, and simultaneously for directly controlling the noise removal means with a gate signal to operate on the electro-cardiographic waves at the known timings.

2. The apparatus of claim 1, wherein the noise removal means comprises a sample and hold circuit.

3. The apparatus of claim 2, wherein the sample and hold circuit comprises means for holding the electro-cardiographic waves during periods of RF pulse application, and for sampling the electro-cardiographic waves otherwise.

4. The apparatus of claim 1, wherein the imaging means measures a time for each of the collection timings with respect to a latest one of the synchronization signals, memorizes the measured time along with an encode condition at said each one of the collection timings, and selects the nuclear magnetic resonance signals of equivalent heart beat phase from the collected nuclear magnetic resonance signals by using the measured time and the encode condition in reconstructing the nuclear magnetic resonance images.

5. The apparatus of claim 4, wherein the imaging means collects the nuclear magnetic resonance signals in a non-gate mode.

6. A method of nuclear magnetic resonance imaging, comprising the steps of:

obtaining electro-cardiographic waves from a patient;

removing external noises from the electro-cardiographic waves by operating on the electro-cardiographic waves to obtain noise removed electro-cardiographic waves;

generating synchronization signals in correspondence to the noise removed electro-cardiographic waves;

taking nuclear magnetic resonance images by collecting nuclear magnetic resonance signals from the patient at collection timings determined in correspondence to the synchronization signals, and by reconstructing the nuclear magnetic resonance images by using the collected nuclear magnetic resonance signals; and controlling an operation for taking the nuclear magnetic resonance images at the taking step according to a prescribed sequence in which the external noises are generated at known timings, and simultaneously directly controlling an operation by sending a gate signal for removing the external noises at the removing step to operate on the electro-cardiographic waves at the known timings.

7. The method of claim 6, wherein the removing step further includes the step of sampling and holding the electro-cardiographic waves using a sample and hold circuit.

8. The method of claim 7, wherein the removing step further includes the steps of: holding the electro-cardiographic waves during periods of RF pulse application in the precribed sequence, and sampling the electro-cardiographic waves otherwise.

9. The method of claim 6, wherein the taking step further includes the steps of:

measuring a time for each of the collection timings with respect to a latest one of the synchronization signals;

memorizing the measured time along with encode condition at said each one of the collection timings; and selecting the nuclear magnetic resonance signals of equivalent heart beat phase from the collected nuclear magnetic resonance signals by using the measured time and the encode condition in reconstructing the nuclear magnetic resonance images.

10. The method of claim 9, wherein the taking step further includes the step of collecting the nuclear magnetic resonance signals in a non-gate mode.

* * * * *